US005299464A

United States Patent [19]

Bennett

[11] Patent Number: 5,299,464

[45] Date of Patent: Apr. 5, 1994

[54] HOT STICK TRANSFORMER SAMPLER

[76] Inventor: James A. Bennett, 1025 Dodson Rd. NW, Ephrata, Wash. 98823

[21] Appl. No.: 796,593

[22] Filed: Nov. 22, 1991

[51] Int. Cl.[5] .................... G01N 1/10

[52] U.S. Cl. .................... 73/864.74; 73/863.81; 73/863.84; 137/315

[58] Field of Search .......... 73/864.74, 863.81, 863.83, 73/863.84, 863.85, 864.73; 137/315

[56] References Cited

U.S. PATENT DOCUMENTS

| | | | |
|---|---|---|---|
| 1,795,430 | 3/1931 | Howie et al. | 137/318 |
| 3,412,613 | 11/1968 | Brown et al. | 73/864.74 X |
| 3,992,155 | 11/1976 | Nilsson | 137/99 X |
| 4,046,013 | 9/1977 | Green | 73/863.85 X |
| 4,056,981 | 11/1977 | Kalka et al. | 73/863.85 |
| 4,058,373 | 11/1977 | Kurz et al. | 73/19.1 X |
| 4,081,112 | 3/1978 | Chong | 222/391 |
| 4,350,052 | 9/1982 | Kendall | 73/863.86 |
| 4,715,236 | 12/1987 | Willert | 73/863.86 |
| 4,794,327 | 12/1988 | Fernandes | 324/127 X |
| 5,131,283 | 7/1992 | Canfield | 73/864.74 |

FOREIGN PATENT DOCUMENTS 264293 1/1989 Fed. Rep. of Germany ... 73/863.81

OTHER PUBLICATIONS

*Electrical World,* vol. 185, No. 10, p. 72, May 15, 1976 "Transformer-gas Sampling procedure improved"; E. Brame, in 73/863.81.

*Primary Examiner*—Tom Noland
*Attorney, Agent, or Firm*—David L. Tingey

[57] ABSTRACT

A hot-stick with a selective transformer-penetration tool is described. The tool combination is useful for remote sampling of oil from an energized high-voltage utility transformer without introducing an environmental and maintenance risk. The sample is then independently tested for PCB contamination. The tool used in combination with the hot-stick is selected from among a remote drill chuck provided for drilling a guide hole in the transformer, an impalement spike for enlarging the guide hole, a remote syringe to withdraw an oil sample from the transformer, a remote rivet setter, and a remote caulking gun to close and seal the hole.

7 Claims, 5 Drawing Sheets

HOT STICK TRANSFORMER SAMPLER

BACKGROUND OF THE INVENTION

The present invention relates generally to remote testing of energized, high voltage utility transformers and, more specifically, to an assembly tool and procedure for remotely penetrating a utility transformer, extracting oil therefrom for analysis, and resealing the transformer.

In recent years the presence of PCB's used in high voltage utility transformers has been of concern. When PCB's are discovered in the cooling oil of the transformer, the transformer is replaced. With the large number of utility transformers in service, problems in testing has become an issue as much as the actual detection and removal of PCB-contaminated units.

Prior to this invention, before utility transformers were tested, power to the transformer was interrupted. After interrupting power to a transformer, a hole was typically drilled near the base of the transformer, and a small amount of oil was drained out. The hole was then closed with a plug. Typically, the plug was effective only for a limited period of time; normal vibrations such as from 60-cycle a.c. electrical power and from passing motor vehicles would cause the plug to loosen and leak, causing a major environmental and cost concern of utility companies.

Deenergizing the transformer by interrupting power to a power grid causes customer dissatisfaction and risks liability for failures caused in facilities that were not sufficiently notified or given adequate time to prepare. With a growing number of facilities dependent on computer processors and other similar equipment, maintaining continuous power is a high priority. It is therefore much preferred to have a oil-sampling system that does not require power interruption to the transformer. However, industry rules require that operators remain at least 24 inches from any energized high voltage utility transformer to minimize danger to the operator. Any tool used by an operator inside that protective distance must provide for electrical insulation of the operator from the tool. Therefore, any procedure for sampling oil from an energized utility transformer must employ a electrically insulating tool or tool system that can be operated at 24 inches from the transformer.

It is therefore an object of the present invention to provide a tool and procedure for facilitating the extraction of oil samples from energized utility transformers.

Another object of the invention is to provide a tool that enables a workman to safely extract oil from an energized transformer by operating the tool a safe distance from the transformer.

Still another object of the invention restore the long-term integrity of the utility transformer after oil is extracted.

A final object is to extract transformer oil without potentially introducing a costly maintenance and environmental problem.

The above objects are attained in the present invention in a hot-stick utility transformer combination selective tool for remote use by an operator for penetrating a utility transformer above the oil line within the transformer, extracting an oil sample with a syringe element, and closing and resealing the transformer.

SUMMARY OF THE INVENTION

A hot-stick with a selective transformer penetration-tool is provided for use in remote sampling of oil from an energized high voltage utility transformer. The sample is then used in testing for PCB contamination. The invention provides a combination tool that obtains transformer without introducing an environmental and maintenance risk. The tool used in combination with the hot-stick is selected from among a remote drill chuck provided for drilling a guide hole in the transformer, an impalement spike for enlarging the guide hole, a remote syringe to withdraw an oil sample from the transformer, a remote rivet setter, and a remote caulking gun to close and seal the hole.

DESCRIPTION OF THE PREFERRED EMBODIMENTS

Referring to the Figures, an elongate, electrically-insulating member 10, commonly known as a "hot-stick," is provided in combination with a detachable selective tool for remotely penetrating and extracting oil from an energized high-voltage utility transformer. The extracted oil sample is then separately tested for possible PCB contamination in the transformer.

Figure 1:
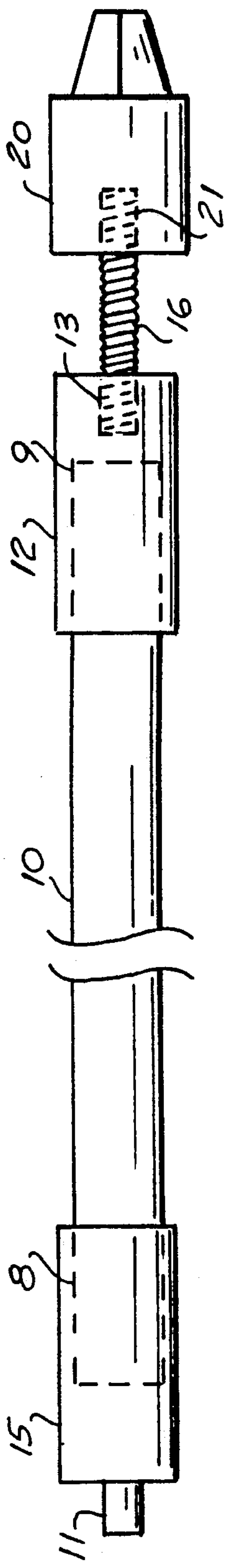
FIG. 1 is a side view of the hot-stick with detachable tool in a first embodiment showing a hot-stick in combination with a keyless chuck as the detachable tool.

FIG. 1 shows the hot-stick 10 with first and second opposite ends 8 and 9 in combination with a keyless chuck 20 in which a small drill can be mounted for penetrating the transformer 5 with a guide hole 6. A hot-stick cap 15 with a drill post 11 extending coaxially from the cap may be secured over the first end 8 of the hot-stick 10, the drill post 11 adapting the hot-stick for mounting in a standard drill chuck. A hot-stick tool attachment end-piece 12 having a threaded hole 13 in its end is secured over the second end 9 of the hot-stick 10 to provide a mounting position of material more durable than that of the hot-stick, which is typically a hardened resin material. In an alternative embodiment, the tool attachment end-piece has a threaded post 16 extending çoaxially therefrom as an alternate tool-mounting configuration in lieu of the threaded hole 13. The detachable selective tool is mounted to the hot-stick tool attachment end-piece 12 in the threaded hole 13 or on the threaded post 16. FIG. i shows the keyless chuck 20 with a threaded hole 21 matching the threaded post 16.

Figure 2:
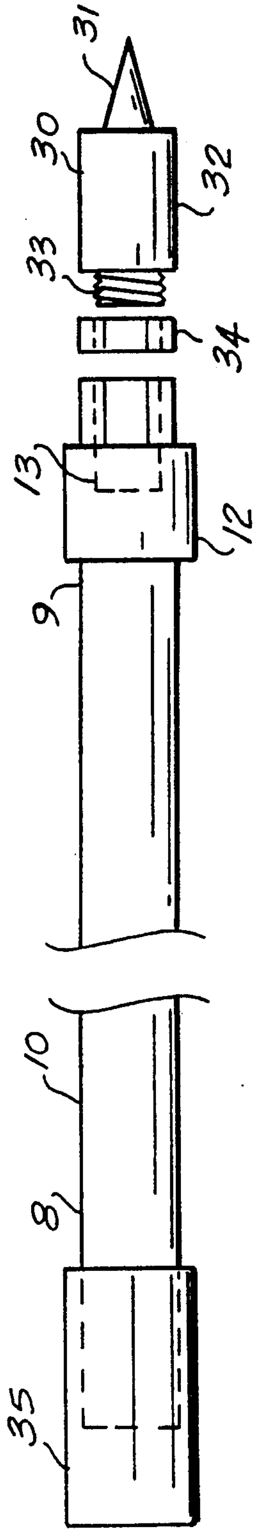
FIG. 2 is a side view of the hot-stick with detachable tool in a second embodiment showing a hot-stick in combination with an impalement spike on an impact block.

FIG. 2 shows the hot-stick 10 in combination with a impalement tool 30 comprising a spike 31 on an impact block 32 and a threaded rod 33 matching the hot-stick threaded hole 13. The impact block 32 is radially larger than the threaded rod 33 and is in face-to-face contact with the hot-stick end-piece 12 so that impulse propagated through the hot-stick is transmitted from the end-piece 12 to the impact block 32. In the alternative, a nut 34 may be used on the threaded rod 33 to better provide contact between the end-piece 12 and the impact block 31. An impact head piece 35 may be added over the first end 8 of the hot-stick 10 to receive impact, for example, from a hammer, to protect the relatively soft hot-stick material.

Figure 3:
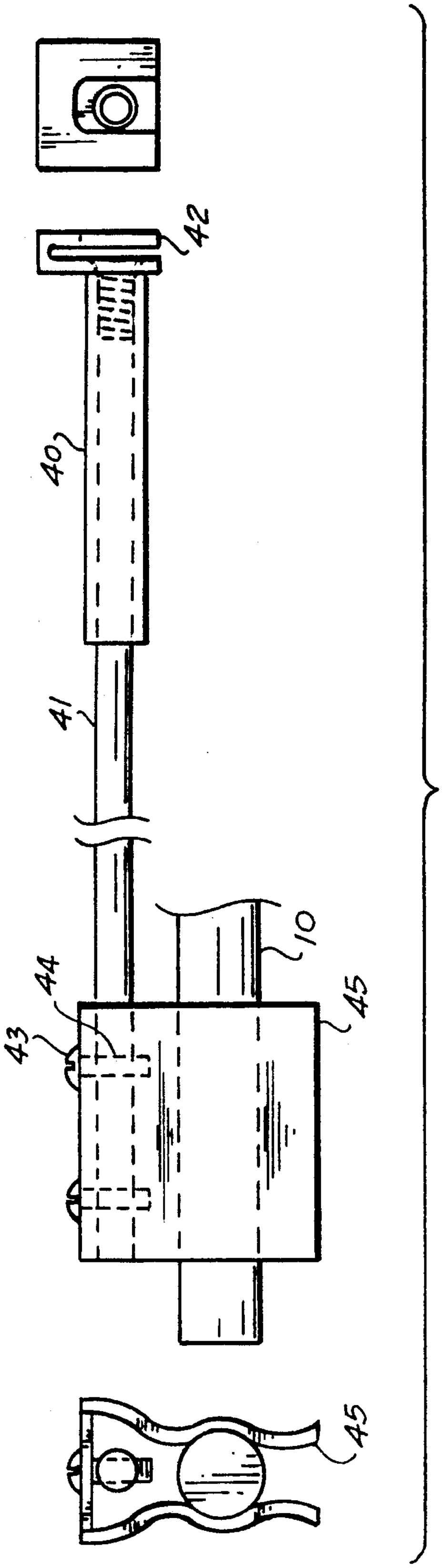
FIG. 3 is a side view of the hot-stick with detachable tool in a third embodiment showing a hot-stick in combination with a syringe extension bar, a syringe clip secured to the first end of the extension bar for attaching the extension bar to ta syringe and a hot-stick clasp for slidable attachment of the extension bar to the hot-stick.

FIG. 3 shows the hot-stick 10 in combination with a syringe extension tool 40 comprising an extension bar 41 with first and second opposite ends, a syringe clip 42 secured to a first end of the extension bar 41, for example by a screw through the syringe clip 42 and into the extension bar 41. A hot-stick clasp 45 is secured to a second end of the extension bar 41, for example by screws 43 in threaded holes 44 transverse in the extension bar 41. The clasp 45 is then slidably mounted over hot-stick 10.

Figure 4:
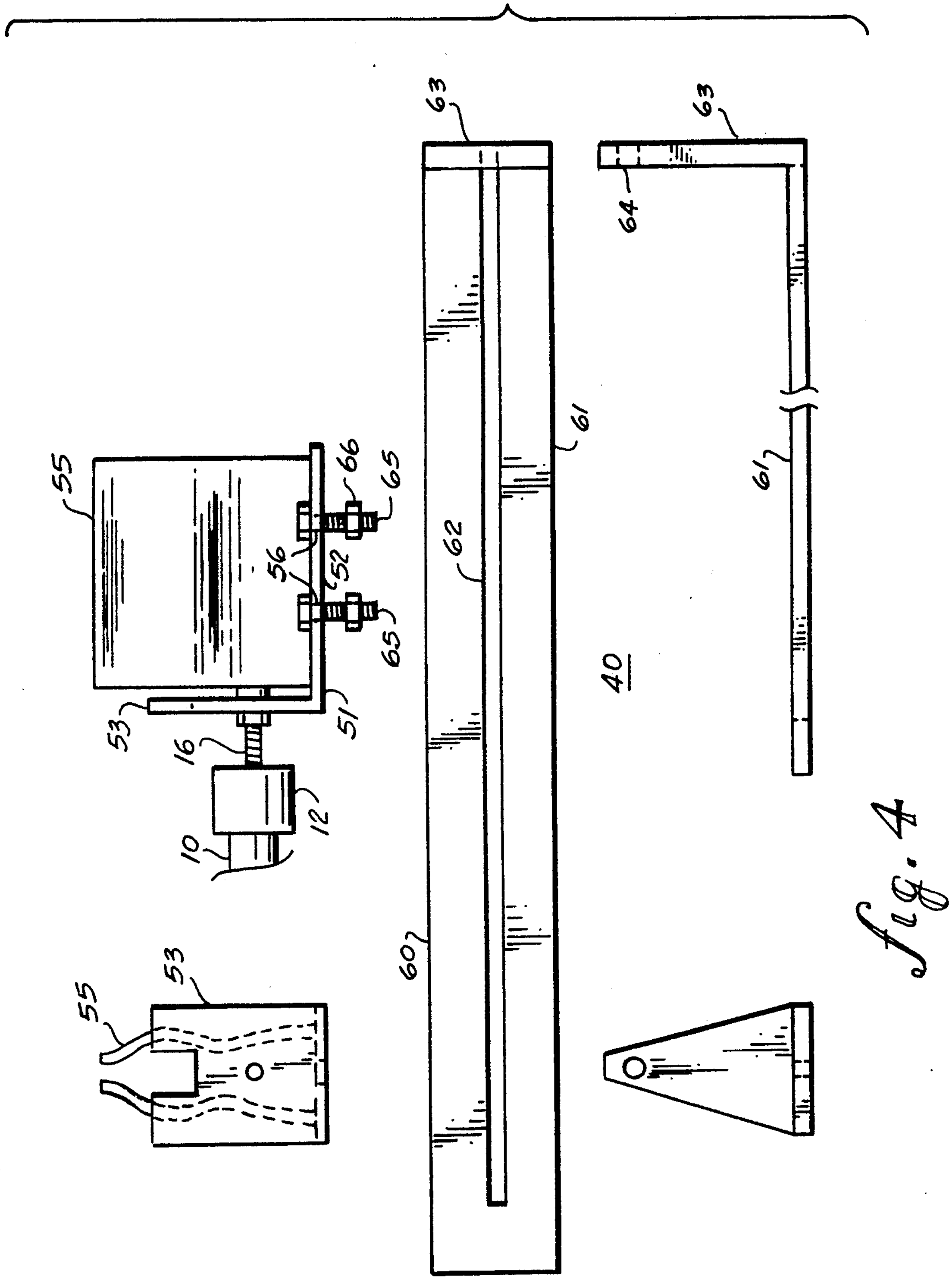
FIG. 4 is a side view of the hot-stick with detachable tool in a fourth embodiment showing a hot-stick in combination with a syringe bracket with a syringe clasp which slides on a slide base.

FIG. 4 further shows a remote syringe tool 40 further comprising a syringe bracket 51 itself comprising a bottom plate 52 and front plate 53 mounted to hot-stick end-piece threaded rod 16. Mounted on the bottom plate 52 is a syringe clasp 55 for holding a removable syringe 54 which may extend over the front plate 53. Mounting holes 56 are also provided in the bottom plate 52. A slide base 60 is provided comprising a slide plate 6 with a longitudinal center slot 62 and a back plate 63 with a hole 64 therethrough for receiving a syringe tube 57. Bolts 65 loosely secured by nuts 66 passing through slide base longitudinal center slot 62 and mounting holes 56 slidably mount the clasp 55 to the slide base 60.

It can be seen that in operation of the hot-stick 10 in combination with the remote syringe tool 40, a conventional syringe is placed within the syringe clasp 55 with the syringe clip 42 affixed over the head 58 of a syringe plunger 59. The first syringe bracket 51 is also moved on the slide base 60 away from the slide base back plate 63 with the flexible syringe tube 57 extending from the syringe through the hole 64 in the back plate 63.

To extract sample oil from a utility transformer with a hole introduced in it above its oil level, the operator moves the hole 64 of the slide base back plate 61 next to the transformer hole and manipulates the syringe tube 57 into the transformer hole 6. He then pushes base slide 61 on the hot-stick against the transformer 5, causing the syringe mounting bracket 51 to slide on the base slide 61, moving the flexible syringe tube 57 into the transformer 5 and its oil. When the hot-stick clasp 45 is made to slide on the hot-stick 10 away from the syringe 54, the syringe plunger 59 is withdrawn within the syringe 54 and oil is syphoned into the syringe 54. The hot-stick 10 with syringe tool 40 is then removed from the transformer 5.

Figure 5:
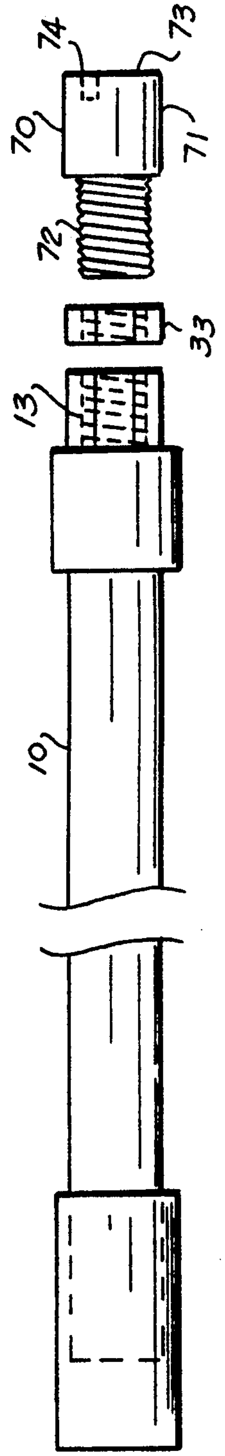
FIG. 5 is a perspective view of the hot-stick with both the syringe extension bar and the syringe bracket on the slide base attached to the hot-stick.

FIG. 5 shows a hot-stick 10 in combination with a rivet setter 70. The rivet setter 70 comprises a setter head 71, a threaded rod 72 matching threaded hole 13 for mounting the rivet setter 70 to the hot-stick 10. As with the impalement tool, the setter head 71 is also radially larger than the threaded rod 72 and is in face-to-face contact with the hot-stick end-piece 12 so that impulse propagated through the hot-stick is transmitted from the end-piece 12 to the impact block. A nut 33 may again be used between the end-piece 12 and the impact head to better transmit the impulse to the setter head 71. The rivet setter further comprises a flat impact surface 73 opposite the threaded rod 72 for transmitting impulse propagated through the hot-stick 10 to a rivet to be set in the hole 6 in the transformer 5. A recess 74 is also provided in the rivet setter flat impact surface 73, offset from its center and sized so that a rivet can be placed in the recess 74 and carried for remotely placing the rivet in the hole 6 in the transformer 5.

Figure 6:
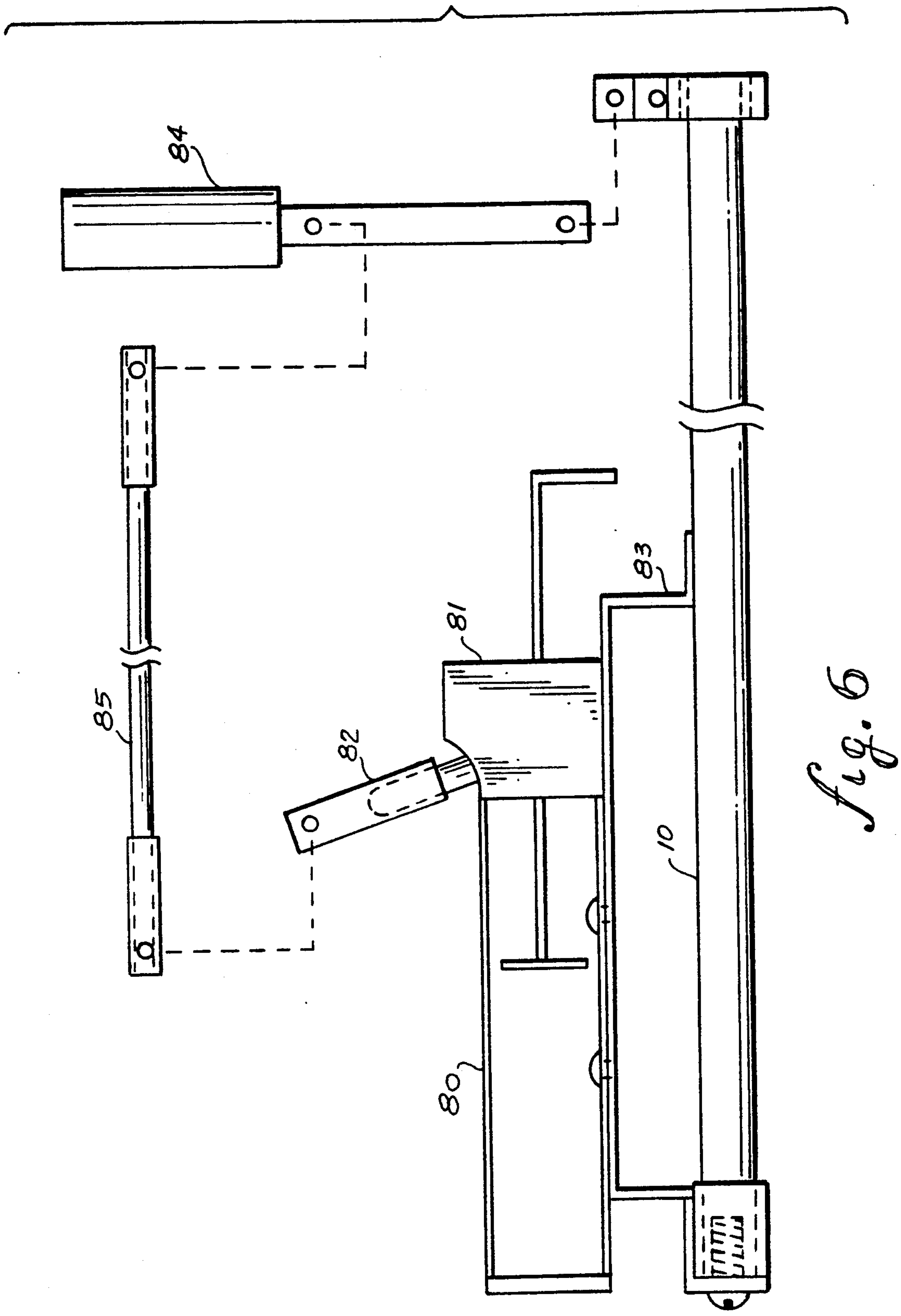
FIG. 6 is a side view of the hot-stick with detachable tool in a fifth embodiment showing a hot-stick in combination with a rivet setter.
Figure 7:
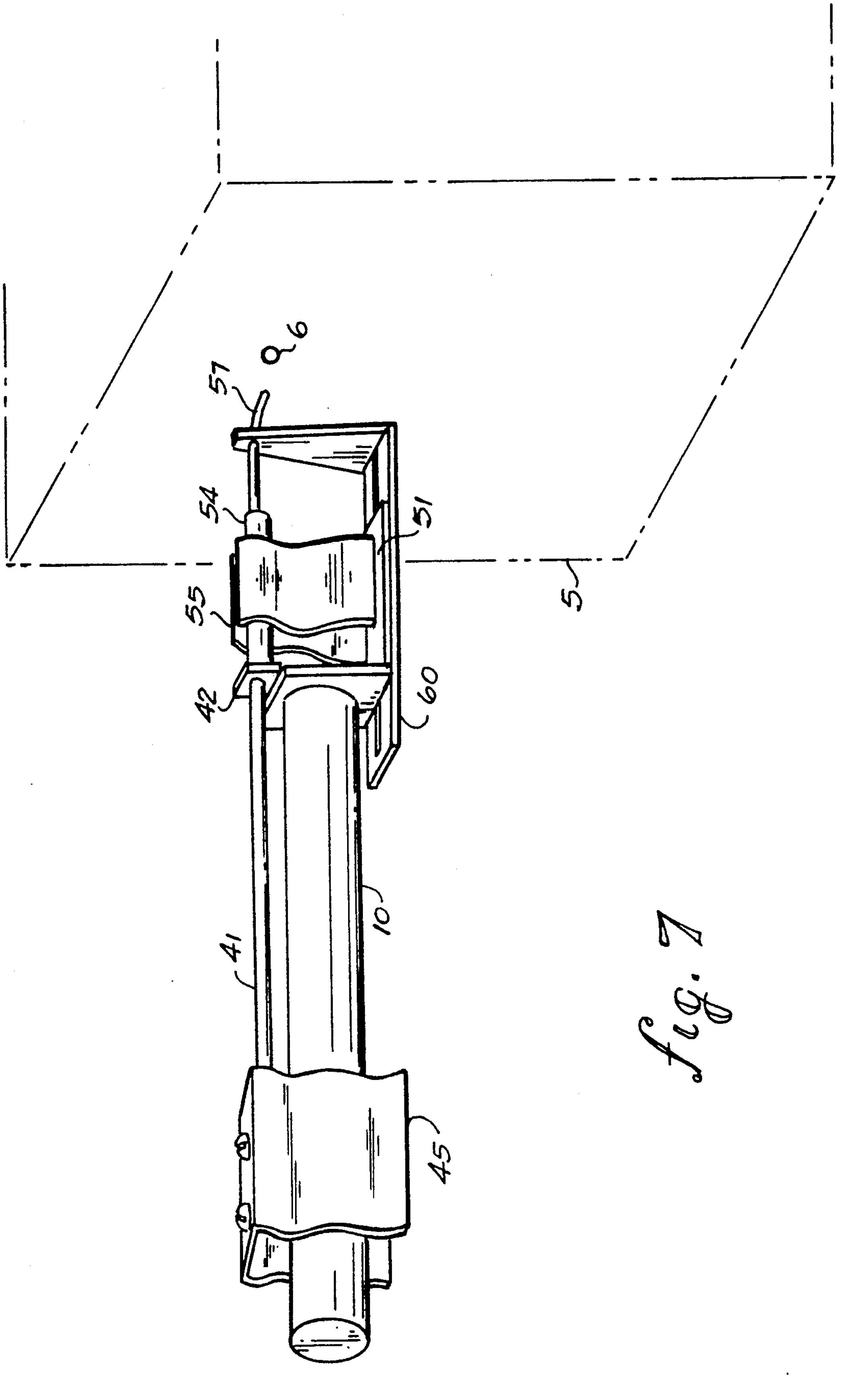
FIG. 7 is a perspective view of the hot-stick with detachable tool in a sixth embodiment showing a hot-stick in combination with a caulk gun mounted to one end of the hot-stick and a remote handle on a caulk gun base attached to the other end.

FIG. 6 shows a hot-stick in combination with a caulking tool 80 comprising a gun mount base mounted to the hot-stick end-piece 12 and the hot-stick 10, a conventional caulking gun 81 such as manufactured by Newborn U.S. Pat. No 4081112) mounted on the gun mount base 83, a caulking gun handle 82, an extension handle 84 pivotably mounted to the hot-stick near its end, an electrically-insulating caulk gun extension bar 83 with first and second opposite ends with its first end pivotably mounted to the caulking gun handle 82 and its second end pivotably mounted to the extension handle 84 intermediate its length. Thus, an operator holding the hot-stick 10 in place can pull the extension handle 84 and the caulk gu handle 82 moving in parallel causes the caulk gun 81 to extrude caulk loaded therein.

Thus, a procedure for extracting oil from an energized high-voltage utility transformer without creating an environmental threat or maintenance problem is to use the hot-stick in combination with a selected tool for penetrating the transformer. Maintaining the required safety distance from the transformer and using only electrically insulated tools remotely, an operator first uses the hot-stick 10 in combination with a keyless chuck 20. A hot-stick sleeve 15 with drill post 11 is mounted on the hot-stick first end 8 and a keyless chuck 20 is mounted on the end-piece 12 at the hot-stick second end 9. With a drill bit in the keyless chuck, the drill post is mounted to and the hot-stick 10 and keyless chuck 20 is driven by a conventional drill to drill a guide hole 6 in the utility transformer 5.

The hot-stick 10 in combination with the impalement tool 30 attached may then be used to enlarge the guide hole 6 by placing the impalement tool spike 31 in the guide hole 6 and hitting the impact head piece 35 on the first end 8 of the hot-stick 10 with a hammer.

The flexible tube 57 of the syringe 54 mounted on the end of the hot-stick is then remotely manipulated into the transformer hole 6 where the tube 57 droops into the transformer oil. Oil is then extracted from the transformer into the syringe when the operator draws the syringe plunger 59 out of the syringe 54 by sliding the hot-stick clasp connected to the syringe head 58 back on the hot-stick.

The syringe is then removed, and the hole 6 is plugged by inserting a rivet into the hole 6 carried in place in the recess 74 of the rivet setter 70. The rivet is then set with the rivet setter impact surface over the rivet by impacting the other end of the hot-stick, such as with a hammer.

The hole 6 and rivet is then sealed with a caulking compound installed remotely with the caulking tool 80 operated from the first end of the hot-stick 10 with the caulking gun mounted on the second end of the hot-stick 10, with appropriate extension members as previously described.

Having described the invention, what is claimed is:

1. A hot-stick with detachable selective transformer-penetrating tool for electrically-isolating an operator from an energized, high voltage utility transformer while sampling oil from the transformer, comprising the combination of
   - an elongate, electrically-insulating member, commonly known as a hot-stick, having first and second opposite ends,
   - a detachable selective transformer-penetrating tool for facilitating the remote sampling of oil from an energized high-voltage utility transformer,
   - wherein the detachable transformer-penetrating tool is a rivet setter further comprising
   - a setter head with first and second impact surface on opposite sides of the setter head, the first impact surface in face-to-face contact with the hot-stick when attached for transmitting impulse propagated through the hot-stick, and
   - the second impact surface becoming a free end for transmitting impulse propagated through the hot-stick to a rivet to be set in a hole in the transformer, and
   - means for attaching the detachable transformer-penetrating tool to the hot-stick.

2. The hot-stock with detachable tool of claim 1 wherein the rivet setter further comprises in its second impact surface offset from its center a rivet-carrying recess into which a rivet can be placed and carried for remotely placing the rivet in a hole in the transformer.

3. A hot-stock with detachable selective transformer-penetrating tool for electrically-isolating an operator from an energized, high voltage utility transformer while sampling oil from the transformer, comprising the combination of
   - an elongate, electrically-insulating member, commonly known as a hot-stick, having first and second opposite ends,
   - a detachable selective transformer-penetrating tool for facilitating the remote sampling of oil from an energized high-voltage utility transformer,
   - wherein the detachable transformer-penetrating tool further comprises
   - an extension bar with first and second opposite ends,
   - a syringe clip secured to the first end of the extension bar for attaching the extension bar to a syringe,
   - a hot-stock clasp secured to the second end of the extension bar, and slidably mounted over the hot-stick,
   - a syringe bracket comprising
     - a bottom plate,
     - a front plate mounted to the tool attachment means of the hot-stick, and
     - a syringe clasp affixed to the bottom plate for holding a removable syringe,
   - a slide base comprising
     - a slide plate with slide means, and
     - means for slidably mounting the syringe bracket on the slide plate slide means, and
   - means for attaching the detachable transformer-penetrating tool to the hot-stick.

4. The hot-stick with detachable tool of claim 3 wherein the slide means of the slide plate further comprises
   - a slide plate having a longitudinal center slot, and
   - wherein the bottom plate has mounting holes therethrough, and
   - wherein the means for slidably mounting the syringe bracket on the slide plate slide means is one or more bolts passing through the slide plate center slot and through the syringe bracket bottom plate mounting holes so that the bolts guide the syringe bracket along the slide plate center slot.

5. The hot-stick with detachable tool of 4 further comprising
   - a back plate on a free end of the slide plate with a hole for receiving a syringe tube to hold the syringe tube while it is manipulated into a transformer hole.

6. A hot-stick with detachable selective tool for electrically-isolating an operator from an energized, high voltage utility transformer while sampling oil from the transformer, comprising the combination of
   - an elongate, electrically-insulating member, commonly known as a hot-stick, having first and second opposite ends,
   - a detachable selective tool for facilitating the remote sampling of oil from an energized high-voltage utility transformer, comprising
   - a caulking gun mount base mounted to the hot-stick second end,
   - a conventional caulking gun mounted on the caulking gun mount base,
   - a caulking gun actuating handle on the caulking gun,
   - an extension handle pivotably mounted to the hot-stick near the hot-stick first end,
   - an electrically-insulating caulking gun extension bar with first and second opposite ends with its first end pivotably mounted to the caulking gun handle and its second end pivotably mounted to the extension handle so that an operator holding the hot-stick in place and pulling the extension handle moves the caulk gun handle in parallel causing the caulking gun to extrude caulk loaded therein, and
   - means for attaching the tool to the hot-stick.

7. A hot-stick with detachable selective transformer-penetrating tool for electrically-isolating an operator from an energized, high voltage utility transformer while sampling oil from the transformer, comprising the combination of
   - an elongate, electrically-insulating member, commonly known as a hot-stick, having first and second opposite ends,
   - a detachable selective transformer-penetrating tool for facilitating the remote sampling of oil from an energized high-voltage utility transformer comprising an impact block in face-to-face contact with the hot-stick when attached for transmitting impulse propagated through the hot-stock, the impact block further comprising an impalement spike extruding coaxially with the hot-stick from the impact block, and
   - means for attaching the detachable transformer-penetrating tool to the hot-stick.

* * * * *